(12) United States Patent
Dahlmann et al.

(10) Patent No.: US 7,341,617 B2
(45) Date of Patent: Mar. 11, 2008

(54) CORROSION AND GAS HYDRATE INHIBITORS HAVING IMPROVED WATER SOLUBILITY AND INCREASED BIODEGRADABILITY

(75) Inventors: Uwe Dahlmann, Heidelberg (DE); Michael Feustel, Koengernheim (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 433 days.

(21) Appl. No.: 10/783,407

(22) Filed: Feb. 20, 2004

(65) Prior Publication Data

US 2004/0164278 A1   Aug. 26, 2004

(30) Foreign Application Priority Data

Feb. 24, 2003   (DE) ................. 103 07 727

(51) Int. Cl.
*B01D 47/00* (2006.01)
(52) U.S. Cl. ............... 95/153; 252/387; 252/390; 252/396; 507/939; 585/15
(58) Field of Classification Search ............. 252/390, 252/392; 507/90; 585/15, 950
See application file for complete search history.

(56) References Cited

U.S. PATENT DOCUMENTS

| | | | |
|---|---|---|---|
| 4,730,079 A | 3/1988 | Hofinger et al. ............ 560/196 |
| 4,997,912 A | 3/1991 | Wirtz et al. ................ 530/232 |
| 5,135,668 A | 8/1992 | Larsen .................... 252/8.555 |
| 5,432,292 A | 7/1995 | Sloan, Jr. .................... 585/15 |
| 5,460,728 A | 10/1995 | Klomp et al. ............... 210/698 |
| 5,600,044 A | 2/1997 | Colle et al. .................. 585/15 |
| 5,648,575 A | 7/1997 | Klomp et al. ................. 585/15 |
| 6,025,302 A | 2/2000 | Pakulski .................... 507/90 |
| 6,102,986 A | 8/2000 | Klug ......................... 95/153 |
| 6,152,993 A | 11/2000 | Klomp ....................... 95/153 |
| 6,177,497 B1 | 1/2001 | Klug et al. ................. 524/376 |
| 6,214,091 B1* | 4/2001 | Klomp ........................ 95/153 |
| 6,261,346 B1 | 7/2001 | Breuer et al. ............ 106/14.15 |
| 6,369,004 B1 | 4/2002 | Klug et al. ................... 507/90 |
| 6,372,918 B1 | 4/2002 | Feustel et al. ............ 548/349.1 |
| 6,379,294 B1 | 4/2002 | Buijs et al. ................. 584/114 |
| 6,566,309 B1 | 5/2003 | Klug et al. ................... 507/90 |
| 2003/0013614 A1 | 1/2003 | Klug et al. ................. 507/200 |
| 2004/0030206 A1 | 2/2004 | Dahlmann et al. ............. 585/15 |
| 2005/0085396 A1* | 4/2005 | Panchalingam et al. .... 507/235 |

FOREIGN PATENT DOCUMENTS

| | | |
|---|---|---|
| DE | 199 20 152 | 10/2000 |
| DE | 199 30 683 | 1/2001 |
| DE | 100 59 816 | 4/2002 |
| DE | 101 14 638 | 5/2002 |
| EP | 0 212 265 | 3/1987 |
| EP | 0 320 769 | 6/1989 |
| EP | 0 446 616 | 9/1991 |
| EP | 0 736 130 | 10/1996 |
| EP | 0 824 631 | 2/1998 |
| EP | 0 914 407 | 5/1999 |
| EP | 0 946 788 | 10/1999 |
| WO | WO 94/12761 | 6/1994 |
| WO | WO 96/08672 | 3/1996 |
| WO | WO 96/41785 | 12/1996 |
| WO | WO 98/23792 | 6/1998 |
| WO | WO 98/23843 | 6/1998 |
| WO | WO 99/13197 | 3/1999 |
| WO | WO 00/78706 | 12/2000 |
| WO | WO 01/09082 | 2/2001 |

\* cited by examiner

*Primary Examiner*—Marc S. Zimmer
(74) *Attorney, Agent, or Firm*—Richard P. Silverman

(57) ABSTRACT

The invention provides the use of compounds of the formula (1)

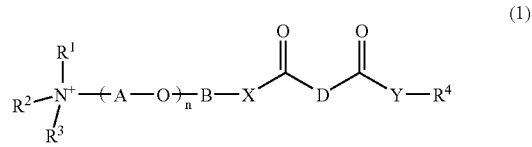

where
$R^1$, $R^2$ are each independently $C_1$- to $C_{22}$-alkyl, $C_2$- to $C_{22}$-alkenyl, $C_6$- to $C_{30}$-aryl or $C_7$- to $C_{30}$-alkylaryl,
$R^3$ is $C_1$- to $C_{22}$-alkyl, $C_2$- to $C_{22}$-alkenyl, $C_6$- to $C_{30}$-aryl or $C_7$- to $C_{30}$-alkylaryl, —$CHR^5$—$COO^-$ or —$O^-$,
$R^4$ is M, hydrogen or an organic radical which optionally contains heteroatoms and has from 1 to 100 carbon atoms,
A is a $C_2$- to $C_4$-alkylene group,
B is a $C_1$- to $C_{10}$-alkylene group,
D is an organic radical which optionally contains heteroatoms and has from 1 to 600 carbon atoms,
X, Y are each independently O or $NR^6$,
$R^5$, $R^6$ are each independently hydrogen, $C_1$- to $C_{22}$-alkyl, $C_2$- to $C_{22}$-alkenyl, $C_6$- to $C_{30}$-aryl or $C_7$- to $C_{30}$-alkylaryl, and
M is a cation
n is a number from 1 to 30
as corrosion inhibitors and gas hydrate inhibitors, and also the compounds of formula 1.

10 Claims, No Drawings

CORROSION AND GAS HYDRATE INHIBITORS HAVING IMPROVED WATER SOLUBILITY AND INCREASED BIODEGRADABILITY

The present invention relates to an additive and to a process for corrosion inhibition and gas hydrate inhibition on and in equipment for extracting and transporting hydrocarbons in crude oil extraction and processing.

In industrial processes in which metals come into contact with water or else with biphasic oil-water systems, there is the risk of corrosion. This is particularly marked when the aqueous phase, as in the case of crude oil production and processing operations, has a high salt content or, as a result of dissolved acidic gases such as carbon dioxide or hydrogen sulfide, is acidic. It is therefore not possible to exploit a deposit and to process crude oil without special additives to protect the equipment used.

Although suitable corrosion protectors for crude oil extraction and processing have been known for some time, they will become unacceptable for offshore applications in the future for reasons of environmental protection.

As typical prior art corrosion inhibitors, amides, amido amines and imidazolines of fatty acids and polyamines have extremely good oil solubility and are therefore only present in the corrosive aqueous phase in low concentration as a consequence of poor partitioning equilibria. Accordingly, these products have to be used in high dosage despite their poor biodegradability.

DE-A-199 30 683 describes corresponding amido amines/imidazolines which are obtained by reacting alkylpolyglycol ether carboxylic acids with polyamines and which, as a consequence of better partitioning, can be used in low concentrations.

Quaternary alkylammonium compounds (quats) constitute alternative prior art corrosion protectors which have not only corrosion-inhibiting but also biostatic properties. Despite improved water solubility, the quats, in comparison to the imidazolines for example, exhibit distinctly reduced film persistence and therefore likewise lead to effective corrosion protection only in high dosage. The strong algae toxicity and the moderate biodegradability restrict the use of quats ever more to ecologically insensitive fields of application, for example onshore.

EP-B-0 946 788 describes a process for protecting metal surfaces against corrosion using ester quats which, it is disclosed, have good biodegradability and low aquatic toxicity.

EP-A-0 320 769 discloses optionally quaternized fatty acid esters of oxyalkylated alkylamino alkylenamines and their use as corrosion inhibitors.

EP-B-0 212 265 describes quaternary polycondensates of alkoxylated alkylamines and dicarboxylic acids and their use as corrosion inhibitors and demulsifiers in crude oils.

EP-B-0 446 616 describes ampholytes and betaines based on fatty acid amido alkylamines which have very good corrosion protection and significantly reduced algae toxicity under the given test conditions.

EP-B-0 584 711 discloses esters, amides and imides of alkenylsuccinic acids with alkoxyalkylamines and their metal or ammonium salts as emulsifiers and corrosion inhibitors for metalworking assistants. The use of alkenylsuccinic esters or amido amine quats or corresponding betaines is not described.

Gas hydrates are crystalline inclusion compounds of gas molecules in water which form under certain temperature and pressure conditions (low temperature and high pressure). The water molecules form cage structures around the appropriate gas molecules. The lattice structure formed from the water molecules is thermodynamically unstable and is always stabilized by the incorporation of gas molecules. Depending on pressure and gas composition, these icelike compounds can exist even to above the freezing point of water (up to above 25° C.).

In the crude oil and natural gas industry, great significance attaches in particular to the gas hydrates which form from water and the natural gas constituents methane, ethane, propane, isobutane, n-butane, nitrogen, carbon dioxide and hydrogen sulfide. Especially in modern natural gas extraction, the existence of these gas hydrates constitutes a great problem, especially when wet gas or multiphasic mixtures of water, gas and alkane mixtures are subjected to low temperatures under high pressure. As a consequence of their insolubility and crystalline structure, the formation of gas hydrates leads here to the blockage of a wide variety of extraction equipment such as pipelines, valves or production equipment in which wet gas or multiphasic mixtures are transported over long distances, as occurs especially in colder regions of the earth or on the seabed.

In addition, gas hydrate formation can also lead to problems in the course of the drilling operation to develop new gas or crude oil deposits at the appropriate pressure and temperature conditions by the formation of gas hydrates in the drilling fluids.

In order to prevent such problems, gas hydrate formation in gas pipelines, in the course of transport of multiphasic mixtures or in drilling fluids, can be suppressed by using relatively large amounts (more than 10% by weight, based on the weight of the aqueous phase) of lower alcohols such as methanol, glycol or diethylene glycol. The addition of these additives has the effect that the thermodynamic limit of gas hydrate formation is shifted to lower temperatures and higher pressures (thermodynamic inhibition). However, the addition of these thermodynamic inhibitors causes serious safety problems (flashpoint and toxicity of the alcohols), logistical problems (large storage tanks, recycling of these solvents) and accordingly high costs, especially in offshore extraction.

Attempts are therefore being made today to replace thermodynamic inhibitors by adding additives in amounts of <2% in temperature and pressure ranges in which gas hydrates can form. These additives either delay gas hydrate formation (kinetic inhibitors) or keep the gas hydrate agglomerates small and therefore pumpable, so that they can be transported through the pipeline (agglomerate inhibitors or antiagglomerates). The inhibitors used either prevent nucleation and/or the growth of the gas hydrate particles, or modify the hydrate growth in such a way that relatively small hydrate particles result.

The gas hydrate inhibitors which have been described in the patent literature, in addition to the known thermodynamic inhibitors, are a multitude of monomeric and also polymeric substance classes which are kinetic inhibitors or agglomeration inhibitors. Of particular significance in this context are polymers having a carbon backbone which contain both cyclic (pyrrolidone or caprolactam radicals) and acyclic amide structures in the side groups.

EP-B-0 736 130 discloses a process for inhibiting gas hydrates which entails feeding a substance of the formula

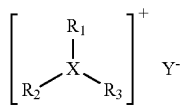

where X=S, N—$R_4$ or P—$R_4$, $R_1$, $R_2$ and $R_3$=alkyl having at least 4 carbon atoms, $R_4$=H or an organic radical, and Y=anion.

This therefore includes compounds of the formula

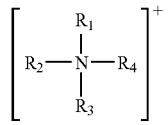

where $R_4$ may be any desired radical, but the $R_1$ to $R_3$ radicals have to be alkyl radicals having at least 4 carbon atoms.

EP-B-0 824 631 discloses a process for inhibiting gas hydrates which entails feeding a substance of the formula

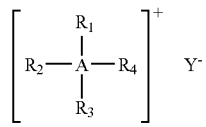

where $R_1$, $R_2$=linear/branched alkyl radicals having 4 or 5 carbon atoms, $R_3$, $R_4$=organic radicals having at least 8 carbon atoms and A=nitrogen or phosphorus. $Y^-$ is an anion. Two of the $R_1$ to $R_4$ radicals have to be linear or branched alkyl radicals having 4 or 5 carbon atoms.

U.S. Pat. No. 5,648,575 discloses a process for inhibiting gas hydrates. The process comprises the use of a compound of the formula

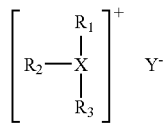

where $R^1$, $R^2$ are linear or branched alkyl groups having at least 4 carbon atoms, $R^3$ is an organic radical having at least 4 atoms, X is sulfur, $NR^4$ or $PR^4$, $R^4$ is hydrogen or an organic radical, and Y is an anion. The document discloses only those compounds which have at least two alkyl radicals having at least 4 carbon atoms.

U.S. Pat. No. 6,025,302 discloses polyetheramine ammonium compounds as gas hydrate inhibitors whose ammonium nitrogen atom, in addition to the polyetheramine chain, bears 3 alkyl substituents.

WO-99/13197 discloses ammonium compounds as gas hydrate inhibitors which have at least one alkoxy group esterified with alkylcarboxylic acids. The advantages of using quaternary dicarboxylic acid derivatives are not disclosed.

WO-01/09082 discloses a process for preparing quaternary amines which, however, bear no alkoxy groups, and their use as gas hydrate inhibitors.

WO-00/078 706 discloses quaternary ammonium compounds as gas hydrate inhibitors which, however, bear no carbonyl radicals.

EP-B-0 914 407 discloses the use of trisubstituted amine oxides as gas hydrate inhibitors.

DE-C-10114638 and DE-C-19920152 describe the use of modified ether carboxamides as gas hydrate inhibitors. The use of quaternized ether carboxylic acid derivatives is not disclosed.

It is an object of the present invention to find novel corrosion inhibitors which, coupled with equally good or improved corrosion protection, offer not only optimum water solubility, more rapid film formation and therefore improved film persistence, but also improved biodegradability in comparison to the prior art corrosion inhibitors.

It is a further object of the present invention to find improved additives which not only slow the formation of gas hydrates (kinetic inhibitors) but also keep gas hydrate agglomerates small and pumpable (antiagglomerates), in order to thus ensure a broad spectrum of application with a high action potential. In addition, it should be possible to replace the thermodynamic inhibitors used currently (methanol and glycols) which cause considerable safety problems and logistical problems.

Prior art gas hydrate inhibitors are commonly coadditivized with corrosion inhibitors, in order to prevent corrosion of the transport and extraction equipment. As a consequence of the frequent lack of immediate compatibility of gas hydrate inhibitor and corrosion protector in the course of formulation, there is additional work for the user. It would be a significant advantage over the prior art if coadditivization with corrosion inhibitors were no longer obligatory.

It has now been found that, surprisingly, quaternary alkylaminoalkyl/alkoxy esters and quaternary alkylaminoalkyl/alkoxy amides of dicarboxylic acids exhibit excellent action as corrosion inhibitors and gas hydrate inhibitors, and also improved film persistence and good biodegradability.

The present invention therefore provides the use of compounds of the formula (1)

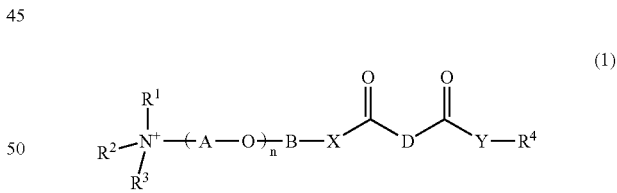

where
- $R^1$, $R^2$ are each independently $C_1$- to $C_{22}$-alkyl, $C_2$- to $C_{22}$-alkenyl, $C_6$- to $C_{30}$-aryl or $C_7$- to $C_{30}$-alkylaryl,
- $R^3$ is $C_1$- to $C_{22}$-alkyl, $C_2$- to $C_{22}$-alkenyl, $C_6$- to $C_{30}$-aryl or $C_7$- to $C_{30}$-alkylaryl, —$CHR^5$—$COO^-$ or —$O^-$,
- $R^4$ is M, hydrogen or an organic radical which optionally contains heteroatoms and has from 1 to 100 carbon atoms,
- A is a $C_2$- to $C_4$-alkylene group,
- B is a $C_1$- to $C_{10}$-alkylene group,
- D is an organic radical which optionally contains heteroatoms and has from 1 to 600 carbon atoms,
- X, Y are each independently O or $NR^6$, $R^5$, $R^6$ are each independently hydrogen, $C_1$- to $C_{22}$-alkyl, $C_2$- to $C_{22}$-alkenyl, $C_6$- to $C_{30}$-aryl or $C_7$- to $C_{30}$-alkylaryl, and M is a cation n is a number from 1 to 30 as corrosion inhibitors and gas hydrate inhibitors.

The invention further provides a method for inhibiting corrosion on metal surfaces, in particular ferrous surfaces, by adding at least one compound of the formula (1) to a corrosive system which is in contact with the metal surfaces.

The invention further provides a method for inhibiting gas hydrates by adding at least one compound of the formula (1) to a system of water and hydrocarbons which tends to the formation of gas hydrates.

The invention further provides the compounds of the formula (1).

For the purposes of this invention, corrosive systems are preferably liquid/liquid or liquid/gaseous multiphase systems consisting of water and hydrocarbons which comprise corrosive constituents, such as salts and acids, in free and/or dissolved form. The corrosive constituents may also be gaseous, for instance hydrogen sulfide and carbon dioxide.

For the purposes of this invention, hydrocarbons are organic compounds which are constituents of the crude oil/natural gas, and their secondary products. For the purposes of this invention, hydrocarbons are also volatile hydrocarbons, for example methane, ethane, propane, butane. For the purposes of this invention, they also include the further gaseous constituents of crude oil/natural gas, for instance hydrogen sulfide and carbon dioxide.

A may be straight-chain or branched and is preferably an ethylene or propylene group, in particular an ethylene group. The alkoxy groups denoted by $(A-O)_n$ may also be mixed alkoxy groups.

B may be straight-chain or branched and is preferably a $C_2$- to $C_4$-alkylene group, in particular an ethylene or propylene group.

$R^1$ and $R^2$ are preferably each independently an alkyl or alkenyl group of from 2 to 14 carbon atoms, in particular those groups having from 3 to 8 carbon atoms and especially butyl groups.

$R^3$ is preferably an alkyl or alkenyl group having from 1 to 12 carbon atoms, in particular having from 1 to 4 carbon atoms.

$R^5$ and $R^6$ are preferably each hydrogen.

n is preferably a number in the range from 1 to 10, more preferably in the range from 2 to 6.

$R^4$ may be any desired organic radical which contains from 1 to 100 carbon atoms and which may optionally contain heteroatoms. When $R^4$ contains heteroatoms, they are preferably nitrogen or oxygen atoms or both, preferably both. The nitrogen atoms may be present in quaternized form.

$R^4$ is preferably a radical of the formula (2)

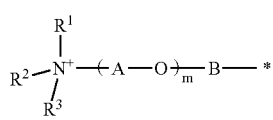

(2)

where $R^1$, $R^2$, $R^3$, A and B are each as defined above with the areas of preference specified above in each case for $R^1$, $R^2$, $R^3$, A and B.

m, independently of n, is a number in the range from 0 to 30, preferably in the range from 1 to 10 and more preferably in the range from 2 to 6.

In a further preferred embodiment, $R^4$ includes hydrogen which may be present either in covalently bound or dissociated form.

D may be any desired bivalent organic radical which may contain from 1 to 600 carbon atoms and which may optionally contain heteroatoms. The bonding of the two carbonyl functions to D is preferably via a free valence of an alkyl or alkenyl group to any desired point on D.

When D contains no heteroatoms, it is preferably a $C_2$- to C50-alkylene or $C_2$- to $C_{50}$-alkenylene group which may be straight-chain or branched, and which is derived from saturated and/or unsaturated dicarboxylic acids, such as adipic acid, succinic acid, maleic acid or malonic acid, more preferably from fatty acids, such as dimeric fatty acids and trimeric fatty acids.

In a further, particularly preferred embodiment, D is $C_6$- to $C_{50}$-aryl or -arylalkyl radicals, in particular radicals which are derived from benzenedicarboxylic acids, more preferably from terephthalic acid (benzene-1,4-dicarboxylic acid).

In a further, preferred embodiment, D is derived from substituted succinic acid derivatives having from 10 to 100 carbon atoms. The substituent bonded to the succinic acid derivative is preferably a $C_2$- to $C_{90}$-alkylene or $C_2$- to $C_{90}$-alkenylene group which is obtainable as an oligomer of $C_2$- to $C_8$-alkenes, and may be straight-chain or branched, and is derived in particular from ethylene, propylene and butylene.

When D contains heteroatoms, they are preferably nitrogen or oxygen atoms or both, preferably both. The nitrogen atoms may be present in quaternized form.

D is preferably a radical of the formula (3)

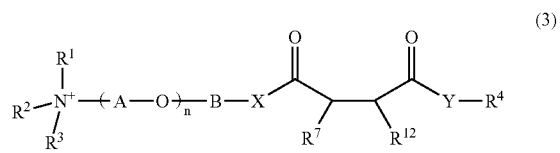

(3)

where $R^7$ and $R^{12}$ are each either hydrogen or a $C_2$- to $C_{100}$-alkyl or $C_2$- to $C_{100}$-alkenyl radical which is obtainable as an oligomer of $C_2$- to $C_8$-alkenes and may be straight-chain or branched, and is derived in particular from ethylene, propylene and butylene, with the proviso that exactly one of the $R^7$ and $R^{12}$ radicals is hydrogen. $R^1$, $R^2$, $R^3$, $R^4$, A, B, X, Y and n are each as already defined above with the areas of preference specified above in each case for $R^1$, $R^2$, $R^3$, $R^4$, A, B, X, Y and n.

In the preferred embodiments of D according to formula (3), the bonding of D according to formula (1) is in each case via a valence of an alkyl or an alkenyl radical at any desired point on $R^7$ or $R^{12}$.

M is a mono- or polyvalent cation, preferably metal ion, more preferably alkali metal or alkaline earth metal ions.

In a further preferred embodiment, M is an ammonium ion of the formula $N^+R^8R^9R^{10}R^{11}$, where $R^8$, $R^9$, $R^{10}$ and $R^{11}$ are each independently hydrogen or any desired organic radical which contains from 1 to 100 carbon atoms, and which may optionally contain heteroatoms. When $R^8$, $R^9$, $R^{10}$ and/or $R^{11}$ contain heteroatoms, they are preferably nitrogen or oxygen atoms or both, preferably both. The nitrogen atoms may be present in quaternized form.

When $R^3$ is $C_1$- to $C_{22}$-alkyl, $C_2$- to $C_{22}$-alkenyl or $C_6$- to $C_{30}$-alkylaryl, suitable counterions for the compounds of formula (1) to (3) are any anions which do not impair the solubility of the compounds of the formula (1) to (3) in the organic-aqueous mixed phases. Such counterions are, for example, methylsulfate ions (methosulfate) or halide ions.

When $R^3$ is —$CHR^5$—$COO^-$ or —$O^-$, the compounds of the formula (1) to (3) are betaines and amine oxides respectively and, as internal salts (ampholytes), have an intramolecular counterion.

The compounds according to the invention can be used alone or in combination with other known corrosion inhibitors and/or gas hydrate inhibitors. In general, sufficient corrosion inhibitor and/or gas hydrate inhibitor according to the invention is used to obtain sufficient corrosion protection and protection from gas hydrate formation under the given conditions.

Preferred use concentrations of the corrosion inhibitors based on the pure compounds of the invention are from 5 to 5 000 ppm, preferably from 10 to 1000 ppm, in particular from 15 to 150 ppm.

The gas hydrate inhibitors are generally used in amounts between 0.01 and 5% by weight of the pure compounds according to the invention based on the aqueous phase, preferably between 0.05 and 2% by weight.

Also particularly suitable as corrosion inhibitors and/or gas hydrate inhibitors are mixtures of the products according to the invention with other prior art corrosion inhibitors and/or gas hydrate inhibitors.

Particularly suitable corrosion inhibitors and therefore a preferred embodiment of this invention are mixtures of the compounds of the formula (1) to (3), such as amido amines and/or imidazolines of fatty acids and polyamines and their salts, quaternary ammonium salts, ethoxylated/propoxylated amines, amphoglycinates and -propionates, betaines or compounds described in DE-A-19930683.

Particularly suitable gas hydrate inhibitors and therefore a preferred embodiment of this invention are mixtures of the compounds of the formula (1) with one or more polymers having a carbon backbone obtained by polymerization and amide bonds in the side chains. These include in particular polymers such as polyvinylpyrrolidone, polyvinylcaprolactam, polyisopropylacrylamide, polyacryloylpyrrolidine, copolymers of vinylpyrrolidone and vinylcaprolactam, copolymers of vinylcaprolactam and N-methyl-N-vinylacetamide, and also terpolymers of vinylpyrrolidone, vinylcaprolactam and further anionic, cationic and neutral comonomers having a vinylic double bond, such as 2-dimethylaminoethyl methacrylate, 1-olefins, N-alkylacrylamides, N-vinylacetamide, acrylamide, sodium 2-acrylamido-2-methyl-1-propanesulfonate (AMPS) or acrylic acid. Also suitable are mixtures with homo- and copolymers of N,N-dialkylacrylamides such as N-acryloylpyrrolidine, N-acryloylmorpholine and N-acryloylpiperidine, or N-alkylacrylamides such as isopropylacrylamide, and also both homo- and copolymers of alkoxyalkyl-substituted (meth) acrylic esters. Likewise suitable are mixtures with alkylpolyglycosides, hydroxyethylcellulose, carboxymethylcellulose and also other ionic or nonionic surfactant molecules.

In a preferred embodiment of the invention, the gas hydrate inhibitors according to the invention are used in a mixture with polymers which are disclosed in WO-A-96/08672. These polymers are those which have structural units of the formula

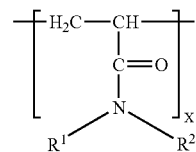

where $R^1$ is a hydrocarbon group having from 1 to 10 carbon atoms and from 0 to 4 heteroatoms selected from N, O and S, $R^2$ is a hydrocarbon group as defined for $R^1$, and X is the average number of the repeating units, the latter being such that the polymer has a molecular weight of from 1 000 to 6 000 000. For use in the context of the present invention, polyisopropylacrylamides and polyacryloylpyrrolidines are particularly suitable.

In a further preferred embodiment of the invention, the gas hydrate inhibitors according to the invention are used in a mixture with polymers which are disclosed in WO-A-96/41785. This document discloses gas hydrate inhibitors including structural units

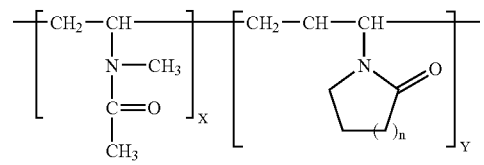

where n is a number from 1 to 3, and x and y are the number of repeating units which is such that the molecular weight of the polymer is between 1 000 and 6 000 000. For use in the context of the present invention, copolymers of N-vinylcaprolactam and N-vinyl-N-methylacetamide or vinylpyrrolidone are particularly suitable.

In a further preferred embodiment of the invention, the gas hydrate inhibitors according to the invention are used in a mixture with other polymers which are disclosed in WO-A-94/12761. The document discloses additives which are for preventing the formation of gas hydrates and contain polymers including cyclic constituents having from 5 to 7 ring members. For use in the context of the present invention, polyvinylcaprolactam, polyvinylpyrrolidone and hydroxyethylcellulose in particular are suitable.

Also particularly suitable are mixtures of the polymers according to the invention with gas hydrate inhibitors based on maleic anhydride, as described in WO-A-97/6506, in particular with maleic anhydride copolymers reacted with mono- and/or diamines. Among these particular preference is given in particular to modified vinyl acetate-maleic anhydride copolymers.

In a further preferred embodiment of the invention, the gas hydrate inhibitors according to the invention are used in a mixture with other polymers which are disclosed in DE-C-10059 816. The document discloses additives which are for preventing the formation of gas hydrates and contain polymers including homo- and also copolymers which contain alkoxyalkyl-substituted (meth)acrylic esters.

When mixtures are used, the concentration ratios between the gas hydrate inhibitors according to the invention and the mixed-in components are from 90:10 to 10:90 percent by weight, and preference is given to mixtures in the ratios from 75:25 to 25:75, and in particular from 60:40 to 40:60.

Like their mixtures with other gas hydrate inhibitors, the compounds can be added to the multiphase mixture which is prone to hydrate formation in the course of crude oil and natural gas extraction or in the course of provision of drilling muds using common equipment such as injection pumps or the like; as a consequence of the good solubility of the polymers according to the invention, there is rapid and uniform distribution of the inhibitor in the aqueous phase or the condensate phase tending to hydrate formation.

The compounds according to the invention can be prepared by reacting alkoxylated alkylamines, alkylaminoalkylenamines or else alkylaminoalkyletheramines with dicarboxylic acid derivatives to give the corresponding mono- or dicarboxylic esters, or mono- or dicarboxamides, optionally to give cyclic dicarboximides, in accordance with the reaction ratios. Subsequently, quaternization is effected using suitable alkylating agents.

The preparation of alkoxylated alkylamines, alkylaminoalkylenamines or else alkylaminoalkyletheramines is described in the prior art.

The alkoxylated alkylamines used are based on dialkylamines having $C_1$- to $C_{22}$-alkyl radicals or $C_2$- to $C_{22}$-alkenyl radicals, preferably $C_3$- to $C_8$-dialkylamines. Suitable dialkylamines are, for example, di-n-butylamine, diisobutylamine, dipentylamine, dihexylamine, dioctylamine, dicyclopentylamine, dicyclohexylamine, diphenylamine, dibenzylamine.

The alkylamines are generally reacted with ethylene oxide, propylene oxide, butylene oxide or mixtures of different such alkylene oxides, although preference is given to ethylene oxide or mixtures of ethylene oxide and propylene oxide. Based on the alkylamines, 1-30 mol of alkylene oxide are added, preferably 1-10 mol, more preferably 2-6 mol.

The alkoxylation proceeds without solvent, but can also be carried out in solution. Suitable solvents for the alkoxylation are inert ethers such as dioxane, tetrahydrofuran, glyme, diglyme and MPEGs.

In general, the alkoxylation is carried out uncatalyzed in the first reaction step up to >95% by weight of tertiary nitrogen. Higher alkoxylation is effected after addition of basic compounds as catalysts. Useful basic compounds are alkali metal/alkaline earth metal hydroxides or alkoxides (sodium methoxide, sodium ethoxide, potassium tert-butoxide), but preference is given to alkali metal hydroxides, particularly sodium hydroxide or potassium hydroxide.

The alkylaminoalkylenamines used are based substantially on dialkylaminoalkylenamines having $C_1$- to $C_{22}$-alkyl radicals or $C_2$- to $C_{22}$-alkenyl radicals, preferably tertiary $C_1$- to $C_8$-dialkylaminoalkylenamines. Particularly suitable are, for example, N,N-dibutylaminopropylamine, N,N-diethylaminopropylamine, N,N-dimethylaminopropylamine, N,N-dimethylaminobutylamine, N,N-dimethylaminohexylamine, N,N-dimethylaminodecylamine, N,N-dibutylaminoethylamine and N,N-dimethylamino-2-hydroxypropylamine.

The dicarboxylic acid derivatives used are based on free dicarboxylic acids, dicarboxylic diesters, dicarboxylic anhydrides and dicarboxylic halides, preferably diesters and anhydrides. Particularly suitable are anhydrides, for example maleic anhydride, succinic anhydride, phthalic anhydride and alkenylsuccinic anhydrides.

The preparation of alkenylsuccinic anhydrides by thermal or catalyzed "ene" reaction is described in the prior art. In this reaction, olefins, preferably olefins having a terminal double bond, are reacted with maleic anhydride under elevated temperatures. Depending on the reaction method, on the type of the olefin used and on the molar ratio used, mono- and/or bisadducts, in some cases polyadducts, are obtained.

The ether dicarboxylic acids on which the invention is based can be prepared by known routes, either by reaction of the terminal —$CH_2OH$ function of a diol reacted with alkylene oxide to give the carboxylic acid, by alkylation with chloroacetic acid derivatives by the Williamson ether synthesis, or by oxidation.

Suitable base alcohols are more preferably $C_2$-$C_{30}$ diols, such as ethylene glycol, propanediols and butanediols which are reacted with alkylene oxides such as ethylene oxide, propylene oxide or butylene oxide, or mixtures thereof, to give corresponding glycol ethers, and particular preference is given to ethylene oxide. The products are reacted preferably with 1-30 mol of alkylene oxide, more preferably 2-6 mol of ethylene oxide.

When mixtures of the alkylene oxides are used, the resulting alkylene glycol alkyl ethers may contain the alkylene glycol units in random sequence and/or as block oligomers.

The ether dicarboxylic acid is prepared from these alkylene glycol alkyl ethers by oxidation with atmospheric oxygen in the presence of catalysts or by oxidation with hypochlorite or chlorite, with and without catalysts.

However, particular preference is given to alkylating the alkylene glycol alkyl ethers with chloroacetic acid derivatives, preferably with sodium chloroacetate and sodium hydroxide solution by the Williamson method. The free carboxylic acid is obtained from the alkaline alkylation mixture by acidifying with mineral acid (hydrochloric, sulfuric acid) and heating above the cloud point and removing the organic phase.

The dicarboxylic acid derivatives are generally reacted with the alkoxylated alkylamines or alkylaminoalkylenamines at 60-240° C., preferably at 120-200° C., in such a way that, optionally in the presence of the dicarboxylic acid derivative used, there is complete condensation to the corresponding mono- or dicarboxylic esters, or mono- or dicarboxamides, in some cases to cyclic dicarboximides, with elimination of water of reaction or of alcohol. The degree of reaction can be followed by determination of the acid number, hydrolysis number and/or by the determination of the base and/or amide nitrogen.

The reaction proceeds without solvent, but can also preferably be carried out in solution. Especially when carboxylic acids are used, it is necessary to use solvents when high conversions and low acid numbers of the resulting reaction products are pursued. Suitable solvents for the preparation are organic compounds which azeotropically remove the water of reaction. In particular, aromatic solvents or solvent mixtures, or alcohols, can be used. Particular preference is given to 2-ethylhexanol. The reaction is then effected at the boiling point of the azeotrope.

When dicarboxylic diamides are prepared, preference is given to using dicarboxylic diester and an excess of the appropriate amine, which can be distillatively removed with the alcohol being released or after the reaction. When dicarboxylic anhydrides are used, preference is given to iteratively fully esterifying with a suitable alcohol and then amidating. Suitable alcohols are, for example, ethanol, propanol, isopropanol or 2-ethylhexanol. Particular preference is given to 2-ethylhexanol.

According to the prior art, the esterifications and amidations can be accelerated by addition of suitable acid catalysts having a p$K_a$ of less than or equal to 5, for example mineral acids or sulfonic acids. Particular preference is given to alkylstannic acids.

For the preparation of the compounds according to the invention, the alkylaminoalkyl/alkoxy esters or alkylaminoalkyl/alkoxy amides are appropriately quaternized in a subsequent reaction step. The quaternization may be effected by appropriate alkylating agents at from 50 to 150° C. Suitable alkylating agents are alkyl halides and alkyl sulfates, preferably methyl chloride, methyl iodide, butyl bromide and dimethyl sulfate.

For the preparation of the betaines according to the invention, reaction is effected with a halocarboxylic acid and a base, preferably chloroacetic acid and sodium hydroxide. This may be effected by initially charging the alkylamino amides with from 50 to 125 mol % of halocarboxylic acid at 40° C. and reacting at from 40 to 100° C. by adding the base and the amount remaining up to 125 mol % of halocarboxylic acid, all at once or in portions.

The basic compounds used may be alkali metal/alkaline earth metal hydroxides or alkoxides (sodium methoxide, sodium ethoxide, potassium tert-butoxide), but preferably alkali metal hydroxides, particularly sodium hydroxide or potassium hydroxide, in particular their aqueous solutions.

The amine oxides according to the invention are prepared by existing prior art processes, preferably by oxidation of the appropriate tertiary amine group with peroxides or peracids, preferably with hydrogen peroxide.

The reactions to give the quaternary alkylaminoalkyl/alkoxy esters or alkylaminoalkyl/alkoxy amides proceed without solvent, but can also preferably be carried out in solution. Suitable solvents for the preparation of quats, betaines and amine oxides are inert alcohols such as isopropanol, 2-ethylhexanol, or inert ethers such as tetrahydrofuran, glyme, diglyme and MPEGs.

Depending on the given requirements, the solvent used may remain in the product according to the invention or has to be removed distillatively.

EXAMPLES

General method for the preparation of alkylaminoalkyl/alkoxy monoesters from dicarboxylic anhydrides A stirred apparatus equipped with a reflux condenser was initially charged with 0.3 mol of the appropriate anhydride (based on hydrolysis number) with nitrogen purging and heated to 60° C. 0.3 mol of the appropriate alkoxylated alkylenediamine (based on OH number) was then added dropwise over 0.5 hour, in the course of which the reaction mixture is heated to approximately 70° C. The reaction mixture was stirred at 60° C. for a further 5 h.

Example 1

N,N-Dibutylamino-N-tri(ethoxy)ethyl dodecenyl-/tetradecenylsuccinate 84.2 g of dodecenyl-/tetradecenylsuccinic anhydride (HN=399.9 mg KOH/g) and 72.9 g of dibutylamine+3.7 EO (OHN=230.9 mg KOH/g) were used to obtain approx. 155 g of N,N-dibutylamino-N-tri(ethoxy)ethyl dodecenyl-/tetradecenylsuccinate having AN=106.6 mg KOH/g and basic N=2.24%.

Example 2

N,N-Dibutylamino-N-tri(ethoxy)ethyl tripropylenesuccinate 74.1 g of tripropylenesuccinic anhydride (HN=454.5 mg KOH/g) and 72.9 g of dibutylamine+3.7 EO (OHN=230.9 mg KOH/g) were used to obtain approx. 145 g of N,N-dibutylamino-N-tri(ethoxy)ethyl tripropylenesuccinate having AN=123.7 mg KOH/g and basic N=2.39%.

Example 3

N,N-Dibutylamino-N-tri(ethoxy)ethyl tetrapropylenesuccinate 87.8 g of tetrapropylenesuccinic anhydride (HN=383.3 mg KOH/g) and 72.9 g of dibutylamine+3.7 EO (OHN=230.9 mg KOH/g) were used to obtain approx. 160 g of N,N-dibutylamino-N-tri(ethoxy)ethyl tetrapropylenesuccinate having AN=115.6 mg KOH/g and basic N=2.18%.

Example 4

N,N-Dibutylamino-N-tri(ethoxy)ethyl pentapropylenesuccinate 102.8 g of pentapropylenesuccinic anhydride (HN=327.6 mg KOH/g) and 72.9 g of dibutylamine+3.7 EO (OHN=230.9 mg KOH/g) were used to obtain approx. 175 g of N,N-dibutylamino-N-tri(ethoxy)ethyl pentapropylenesuccinate having AN=100.5 mg KOH/g and basic N=2.00%.

Example 5

N,N-Dibutylamino-N-tri(ethoxy)ethyl polyisobutenylsuccinate 130.5 g of polyisobutenylsuccinic anhydride (based on PIB 550; HN=257.9 mg KOH/g) and 72.9 g of dibutylamine+3.7 EO (OHN=230.9 mg KOH/g) were used to prepare approx. 200 g of N,N-dibutylamino-N-tri(ethoxy) ethyl polyisobutenyl-succinate having AN=90.8 mg KOH/g and basic N=1.74%.

General method for the preparation of the alkylaminoalkyl/alkoxy diesters from dicarboxylic anhydrides A stirred apparatus equipped with distillation head with condenser was initially charged with 0.3 mol of the appropriate anhydride (based on hydrolysis number) with nitrogen purging and heated to 60° C. 0.6 mol of the appropriate alkoxylated alkylenediamine (based on OH number) was then added dropwise over 0.5 hour, in the course of which the reaction mixture is heated to approx. 70° C. The reaction mixture was then stirred at 60° C. for a further 0.5 h and then heated to 180° C., and water of reaction was distilled off at this temperature for 5 h. Finally, the water of reaction was removed at 200° C. and 200 mbar for 2 h until acid number (AN) of less than 10 mg KOH/g had been attained.

Example 6 bis[(N,N-Dibutylamino-N-tri(ethoxy)ethyl]dodecenyl-/tetradecenylsuccinate 84.2 g of dodecenyl-/tetradecenylsuccinic anhydride (HN=399.9 mg KOH/g) and 145.8 g of dibutylamine+3.7 EO (OHN=230.9 mg KOH/g) were used to obtain approx.

220 g of bis[N,N-dibutylamino-N-tri(ethoxy)ethyl]dodecenyl-/tetradecenyl-succinate having AN=4.3 mg KOH/g, HN=120.1 mg KOH/g and basic N=2.88%.

Example 7 bis[(N,N-Dibutylamino-N-tri(ethoxy)ethyl]tripropylenesuccinate 74.1 g of tripropylenesuccinic anhydride (HN=454.5 mg KOH/g) and 145.8 g of dibutylamine+3.7 EO (OHN=230.9 mg KOH/g) were used to obtain approx. 210 g of bis[N,N-dibutylamino-N-tri(ethoxy)ethyl]tripropylenesuccinate having AN=8.2 mg KOH/g, HN=127.7 mg KOH/g and basic N=2.81%.

Example 8 bis[(N,N-Dibutylamino-N-tri(ethoxy)ethyl]tetrapropylenesuccinate 87.8 g of tetrapropylenesuccinic anhydride (HN=383.3 mg KOH/g) and 145,8 g of dibutylamine+3.7 EO (OHN=230.9 mg KOH/g) were used to obtain approx. 225 g of bis[N,N-dibutylamino-N-tri(ethoxy)ethyl]tetrapropylenesuccinate having AN=8.8 mg KOH/g, HN=115.4 mg KOH/g and basic N=2.54%.

Example 9 bis[(N,N-Dibutylamino-N-tri(ethoxy)ethyl]pentapropylenesuccinate 102.8 g of pentapropylenesuccinic anhydride (HN=327.6 mg KOH/g) and 145.8 g of dibutylamine+3.7 EO (OHN=230.9 mg KOH/g) were used to obtain approx. 240 g of bis[N,N-dibutylamino-N-tri(ethoxy)ethyl]pentapropylenesuccinate having AN=7.7 mg KOH/g, HN=106.7 mg KOH/g and basic N=2.75%.

Example 10 bis[(N,N-Dibutylamino-N-tri(ethoxy)ethyl]polyisobutenylsuccinate 130.5 g of polyisobutenylsuccinic anhydride (based on PIB 550; HN=257.9 mg KOH/g) and 145.8 g of dibutylamine+3.7 EO (OHN=230.9 mg KOH/g) were used to prepare approx. 270 g of bis[N,N-dibutylamino-N-tri(ethoxy)ethyl]polyisobutenyl-succinate having AN=9.5 mg KOH/g, HN=94.9 mg KOH/g and basic N=2.14%.

General method for the preparation of the alkylaminoalkyl/alkoxy diesters from ether dicarboxylic acids A stirred apparatus equipped with distillation head with condenser was initially charged with 0.3 mol of the appropriate ether dicarboxylic acids (based on hydrolysis number), 0.6 mol of the appropriate alkoxylated alkylenediamine (based on OH number) and 0.5% by weight of p-toluenesulfonic acid with nitrogen purging and continuously heated to 160° C. At this temperature, water of reaction was distilled off over 4 h. Finally, the distillation was continued at 200° C. and 150 mbar and the water of reaction was removed until an acid number (AN) of less than 10 mg KOH/g had been attained.

Example 11 bis[N,N-Dibutylamino-N-tri(ethoxy)ethyl]polyglycoldicarboxylate 212.9 g of polyglycoldicarboxylic acid (HN=158.1 mg KOH/g) and 145.8 g of dibutylamine+3.7 EO (OHN=230.9 mg KOH/g) were used to obtain approx. 340 g of bis[N,N-Dibutylamino-N-tri(ethoxy)ethyl]polyglycoldicarboxylate having AN=5.7 mg KOH/g, HN=80.7 mg KOH/g and basic N=1.78%.

Example 12 bis[N,N-Dibutylamino-N-tri(ethoxy)ethyl]3,6,9-trioxaundecanedioate 78.8 g of 3,6,9-trioxaundecanedioic acid (HN=427.3 mg KOH/g) and 145.8 g of dibutylamine+3.7 EO (OHN=230.9 mg KOH/g) were used to obtain approx. 205 g of bis[N,N-dibutylamino-N-tri(ethoxy)ethyl]3,6,9-trioxaundecanedioate having AN=9.1 mg KOH/g, HN=132.9 mg KOH/g and basic N=3.05%.

General method for the quaternization of dimethyl sulfate

A stirred apparatus was initially charged with 0.2 mol (based on basic N) of the appropriate amine with nitrogen purging and heated to 60° C. 0.19 mol of dimethyl sulfate was added dropwise thereto in such a way that the reaction temperature did not exceed 80-90° C. The reaction mixture was subsequently stirred at 90° C. for a further 3 h. This method was used to quaternize the compounds described by examples 1 to 12 (examples 13 to 24, as listed in tables 1 to 4).

Example 25

Polyvinylcaprolactam having MW 5 000 g/mol is mixed in a ratio of 1:1 with the quats of example 1 described by example 13 and terminated in butyldiglycol.

Example 26

Polyvinylcaprolactam having MW 5 000 g/mol is mixed in a ratio of 1:1 with the quats of example 6 described by example 18 and terminated in butyldiglycol.

Effectiveness of the compounds according to the invention as corrosion inhibitors The compounds according to the invention were tested as corrosion inhibitors in th shell wheel test. Coupons of carbon steel (DIN 1.1203 having 15 cm$^2$ surface area) were immersed in a salt water/petroleum mixture (9:1.5% NaCl solution, adjusted to pH 3.5 using acetic acid) and subjected to this medium at a rotation rate of 40 rpm at 70° C. for 24 hours. The dosage of the inhibitor was 50 ppm of a 40% solution of the inhibitor. The protection values were calculated from the mass reduction of the coupons, based on a blank value.

In the table which follows, "comparison 1" refers to a commercial residue amine, quat based on dicocoalkyldimethylammonium chloride and "comparison 2" to a commercial soya fatty acid amidopropyl-N,N-dimethylammonium carboxymethyl betaine described by EP-B-0 446 616 (prior art corrosion inhibitors).

TABLE 1

(SHELL wheel test)

| Example | Corrosion inhibitor | Ø Protection % |
|---|---|---|
| Comparison 1 | Standard quat | 36.0 |
| Comparison 2 | Standard betaine | 75.4 |
| 13 | Quat from example 1 | 92.5 |
| 14 | Quat from example 2 | 94.2 |
| 15 | Quat from example 3 | 93.8 |
| 16 | Quat from example 4 | 93.6 |
| 17 | Quat from example 5 | 88.7 |
| 18 | Quat from example 6 | 93.3 |
| 19 | Quat from example 7 | 94.5 |
| 20 | Quat from example 8 | 91.9 |
| 21 | Quat from example 9 | 93.1 |
| 22 | Quat from example 10 | 90.6 |

The products were also tested in the LPR test (test conditions similar to ASTM D 2776).

TABLE 2

(LPR test)

| | | Protection after [%] | | |
|---|---|---|---|---|
| Example | Corrosion inhibitor | 10 min | 30 min | 60 min |
| Comparison 1 | Standard quat | 53.9 | 61.2 | 73.7 |
| Comparison 2 | Standard betaine | 45.9 | 59.2 | 64.3 |
| 13 | Quat from example 1 | 79.6 | 86.1 | 87.6 |
| 14 | Quat from example 2 | 79.1 | 85.1 | 87.3 |
| 15 | Quat from example 3 | 84.6 | 89.6 | 91.2 |
| 16 | Quat from example 4 | 81.8 | 87.3 | 89.7 |
| 17 | Quat from example 5 | 74.1 | 80.0 | 83.5 |
| 18 | Quat from example 6 | 78.9 | 85.0 | 86.7 |
| 19 | Quat from example 7 | 81.6 | 86.4 | 88.2 |
| 20 | Quat from example 8 | 76.2 | 82.8 | 85.9 |
| 21 | Quat from example 9 | 77.3 | 81.6 | 83.2 |
| 22 | Quat from example 10 | 68.9 | 74.2 | 79.8 |

As can be seen from the above test results, the products according to the invention have very good corrosion protection properties at low dosage and substantially exceed the effectiveness of the prior art inhibitors. As a consequence of their ester and amide structure, the compounds have better biodegradability and can be used at a lower dosage.

Effectiveness of the Compounds According to the Invention as Gas Hydrate Inhibitors To investigate the inhibiting action of the compounds according to the invention, a stirred steel autoclave having temperature control, pressure and torque sensor having an internal volume of 450 ml was used. For investigations of kinetic inhibition, the autoclave was filled with distilled water and gas in a volume ratio of 20:80, and for investigations of agglomerate inhibition, condensate was additionally added. Finally, natural gas was injected at different pressures.

Starting from a starting temperature of 17.5° C., the autoclave was cooled to 2° C. within 2 h, then stirred at 2° C. for 18 and heated back up to 17.5° C. within 2 h. A pressure decrease corresponding to the thermal compression of the gas is observed. When the formation of gas hydrate nuclei occurs during the supercooling time, the pressure measured falls, and an increase in the torque measured and a slight increase in temperature can be observed. Without inhibitor, further growth and increasing agglomeration of the hydrate nuclei lead rapidly to a further increase in the torque. When the mixture is heated, the gas hydrates decompose, so that the starting state of the experimental series is attained.

The measure used for the inhibiting action of the compounds according to the invention is the time from the attainment of the minimum temperature of 2° C. up to the first gas absorption ($T_{ind}$) or the time up to the rise of the torque ($T_{agg}$). Long induction times or agglomeration times indicate action as a kinetic inhibitor. On the other hand, the torque measured in the autoclave serves as a parameter for the agglomeration of the hydrate crystals. The pressure drop measured ($\Delta p$) allows a direct conclusion on the amount of hydrate crystals formed. In the case of a good antiagglomerate, the torque which builds up after formation of gas hydrates is distinctly reduced compared to the blank value. Ideally, the snowlike, fine hydrate crystals form in the condensate phase and do not agglomerate and thus lead to blockage of the installations serving for gas transport and for gas extraction.

Test Results

Composition of the natural gas used:

Gas 1: 79.3% methane, 10.8% ethane, 4.8% propane, 1.9% butane, 1.4% carbon dioxide, 1.8% nitrogen. Supercooling below the equilibrium temperature of hydrate formation at 50 bar: 12° C.

Gas 2: 92.1% methane, 3.5% ethane, 0.8% propane, 0.7% butane, 0.6% carbon dioxide, 2.3% nitrogen. Supercooling below the equilibrium temperature of hydrate formation at 50 bar: 7° C., supercooling at 100 bar: 12° C.

In order to test the effectiveness as agglomerate inhibitors, the test autoclave used above was initially charged with water and white spirit (20% of the volume in a ratio of 1:2) and, based on the aqueous phase, 5 000 ppm of the particular additive were added. At an autoclave pressure of 90 bar using gas 1 and a stirred speed of 5 000 rpm, the temperature was cooled from initially 17.5° C. within 2 hours to 2° C., then the mixture was stirred at 2° C. for 25 hours and heated again. The pressure drop caused by hydrate formation and the resulting torque at the stirrer, which is a measure of the agglomeration of the gas hydrates, were measured.

TABLE 3

(Test as antiagglomerant)

| Example | Gas hydrate inhibitor | Pressure drop $\Delta p$ (bar) | Temperature rise $\Delta T$ (K) | Torque $M_{max}$ (Ncm) |
|---|---|---|---|---|
| Blank value | — | >40 | >8 | 15.9 |
| 13 | Quat from example 1 | 15.2 | 1.1 | 4.9 |
| 18 | Quat from example 6 | 10.3 | 0.5 | 0.5 |
| 23 | Quat from example 11 | 14.7 | 1.0 | 1.0 |
| 24 | Quat from example 12 | 13.9 | 1.0 | 0.8 |
| Comparison 3 | TBAB | 21.5 | 1.0 | 1.5 |
| Comparison 4 | TBAB | 15.0 | 1.0 | 1.2 |

The comparison substances 3 and 4 used were two commercially available antiagglomerant inhibitors based on tetrabutylammonium bromide (TBAB).

As can be seen from these examples, the torques measured were greatly reduced in comparison to the blank value despite severe hydrate formation. This supports a distinct agglomerate-inhibiting action of the products according to the invention.

In order to test the effectiveness as additives for kinetic inhibitors, 5 000 ppm of the particular additive, based on the aqueous phase, were added in the above-described test autoclave and cooled at different pressures using gases 1 or 2. On attainment of the minimum temperature of 2° C., the time until the first gas absorption ($T_{ind}$) was recorded. The pressure drop ($\Delta p$) and the temperature rise $\Delta T$ (K) allow the amount of hydrate crystals formed to be concluded directly.

TABLE 4

(Test as kinetic inhibitors)

| Example | Inhibitor | Gas | Pressure p (bar) | $T_{ind}$ | Pressure drop $\Delta p$ (bar) | Temperature rise $\Delta T$ (K) |
|---|---|---|---|---|---|---|
| Blank value | — | 1 | 50 | 0 | >40 | >1.5 |
| Blank value | — | 2 | 100 | 0 | >40 | >1.5 |
| 25 | Quat from example 1 | 1 | 50 | 8.0 h | 7.2 | 0.4 |
| 25 | Quat from example 1 | 2 | 100 | <5 min | 10.8 | 0.4 |
| 26 | Quat from example 6 | 1 | 50 | 6.5 h | 9.5 | 0.1 |
| 26 | Quat from example 6 | 2 | 100 | <5 min | 10.1 | 0.2 |
| Comparison 5 | PVCap | 1 | 50 | <5 min | 10 | 0.4 |
| Comparison 5 | PVCap | 2 | 100 | <5 min | 6 | 0.1 |

The comparison substance 5 used was a solution of polyvinylcaprolactam (PVCap) in butylglycol, molecular weight 5 000 g/mol.

As can be recognized from the above test results, the products according to the invention act as a synergistic component of kinetic hydrate inhibitors and exhibit a distinct improvement compared to the prior art. They can therefore be used for increasing (synergistic effect) the performance of prior art inhibitors.

The following abbreviations have been used:

AN=acid value (alternatively "acid number")

HN=saponification value (alternatively "saponification number")

OHN=hydroxyl value (alternatively "hydroxyl number")

AS content=content of active matter

What is claimed is:

1. A method for inhibiting corrosion and gas hydrate formation, said method comprising adding to a mixture of hydrocarbons and water a compound of formula (1)

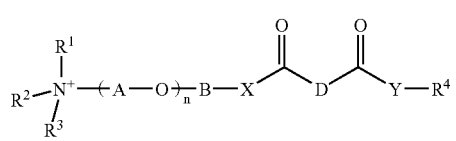

(1)

where $R^1$, $R^2$ are each independently $C_1$- to $C_{22}$-alkyl, $C_2$- to $C_{22}$alkenyl, $C_6$- to $C_{30}$-aryl or $C_7$- to $C_{30}$-alkylaryl, $R^3$ is $C_1$- to $C_{22}$-alkyl, $C_2$- to $C_{22}$-alkenyl, $C_6$- to $C_{30}$-aryl or $C_7$- to $C_{30}$-alkylaryl, —$CHR^5$—$COO^-$ or —$O^-$, $R^4$ is a radical of the formula (2)

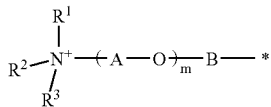

(2)

m is a number from 0 to 30,

A is a $C_2$- to $C_4$-alkylene group,

B is a $C_1$- to $C_{10}$-alkylene group,

D is an organic radical optionally containing heteroatoms and has from 1 to 600 carbon atoms, said organic radical being selected from the group consisting of a straight-chain or branched $C_2$- to $C_{50}$-alkylene group or a straight-chain or branched $C_2$- to $C_{50}$-alkenylene group which is derived from a saturated or unsaturated dicarboxylic acid, a $C_6$- to $C_{50}$-aryl radical or a $C_6$- to $C_{50}$-arylalkyl radical which is derived from a benzenedicarboxylic acid, and a radical of formula (3)

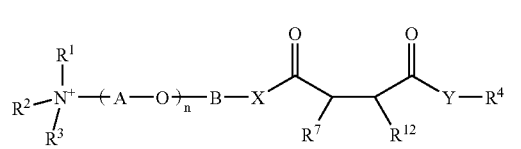

(3)

where $R^7$ and $R^{12}$ are each either hydrogen or a $C_2$- to $C_{100}$-alkyl or $C_2$- to $C_{100}$-alkenyl radical and wherein bonding of D occurs through any valence within $R^7$ or $R^{12}$ X, Y are each independently O or $NR^6$, $R^5$, $R^6$ are each independently hydrogen, $C_1$- to $C_{22}$-alkyl, $C_2$- to $C_{22}$-alkenyl, $C_6$- to $C_{30}$-aryl or $C_7$- to $C_{30}$-alkylaryl, and n is a number from 1 to 30.

2. The method of claim 1, wherein A is an ethylene or propylene group.

3. The method of claim 1, wherein B is a $C_2$- to $C_4$-alkylene group.

4. The method of claim 1, wherein $R^1$ and $R^2$ are each independently an alkyl or alkenyl group of from 2 to 14 carbon atoms.

5. The method of claim 1, wherein $R^3$ is an alkyl or alkenyl group having from 1 to 12 carbon atoms.

6. The method of claim 1, wherein $R^5$ and $R^6$ are hydrogen.

7. The method of claim 1, wherein n is a number in the range from 1 to 10.

8. The method of claim 1, wherein D is a $C_2$- to $C_{50}$-alkylene or $C_2$- to $C_{50}$-alkenylene group.

9. The method of claim 1, wherein D is derived from a substituted succinic acid derivative having from 10 to 100 carbon atoms.

10. The method of claim 1, wherein D is a radical of the formula (3)

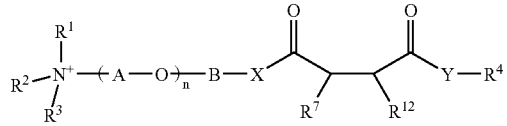
(3)

where
R$^7$ and R$^{12}$ are each either hydrogen or a C$_2$- to C$_{100}$-alkyl or C$_2$- to C$_{100}$-alkenyl radical which is obtainable as an oligomer of C$_2$- to C$_8$-alkenes and may be straight-chain or branched, with the proviso that exactly one of the R$^7$ and R$^{12}$ radicals is hydrogen wherein bonding of D occurs through any valence within R$^7$ or R$^{12}$, and R$^1$, R$^2$ are each independently C$_1$- to C$_{22}$-alkyl, C$_2$- to C$_{22}$-alkenyl, C$_6$- to C$_{30}$-aryl or C$_7$- to C$_{30}$-alkylaryl, R$^3$ is C$_1$- to C$_{22}$-alkyl, C$_2$- to C$_{22}$-alkenyl, C$_6$- to C$_{30}$-aryl or C$_7$- to C$_{30}$-alkylaryl, —CHR$^5$—COO$^-$ or —O$^-$, R$^4$ is a radical of the formula (2)

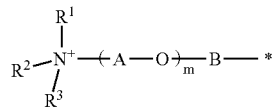
(2)

A is a C$_2$- to C$_4$-alkylene group,
B is a C$_1$- to C$_{10}$-alkylene group,
X, Y are each independently O or NR$^6$,
n is a number from 1 to 30.

* * * * *